United States Patent
Benz et al.

(10) Patent No.: US 7,947,796 B2
(45) Date of Patent: May 24, 2011

(54) MATERIALS FOR MAKING HYDROPHOBIC INTRAOCULAR LENS

(75) Inventors: Patrick H. Benz, Sarasota, FL (US); Jose A. Ors, Sarasota, FL (US)

(73) Assignee: Benz Research & Development Corporation, Sarasota, FL (US)

( * ) Notice: Subject to any disclaimer, the term of this patent is extended or adjusted under 35 U.S.C. 154(b) by 88 days.

(21) Appl. No.: 11/416,351

(22) Filed: May 1, 2006

(65) Prior Publication Data

US 2006/0199929 A1   Sep. 7, 2006

Related U.S. Application Data

(62) Division of application No. 10/981,764, filed on Nov. 5, 2004, now Pat. No. 7,067,602.

(60) Provisional application No. 60/610,195, filed on Sep. 16, 2004, provisional application No. 60/517,107, filed on Nov. 5, 2003.

(51) Int. Cl.
*C08F 120/26* (2006.01)

(52) U.S. Cl. .................. 526/320; 526/323.1; 526/323.2; 526/328.5; 526/329.6; 623/6.11; 623/6.59; 351/160 R; 351/160 H

(58) Field of Classification Search .................. 526/320, 526/323.1, 323.2, 328.5, 329.6; 623/6.11, 623/6.59; 351/160 R, 160 H
See application file for complete search history.

(56) References Cited

U.S. PATENT DOCUMENTS

| | | | |
|---|---|---|---|
| 4,093,361 A * | 6/1978 | Erickson et al. ........... 351/160 R |
| 4,718,906 A | 1/1988 | Mackool | |
| 4,764,169 A | 8/1988 | Grendahl | |
| 5,104,954 A | 4/1992 | Mueller | |
| 5,326,506 A | 7/1994 | Vanderbilt | |
| 6,267,784 B1 | 7/2001 | Benz et al. | |
| 6,329,485 B1 * | 12/2001 | Vanderbilt ................. 526/318.1 |
| 6,517,750 B2 | 2/2003 | Benz et al. | |
| 6,613,857 B1 | 9/2003 | Koch et al. | |
| 7,083,645 B2 * | 8/2006 | Mentak ........................ 623/6.58 |

* cited by examiner

*Primary Examiner* — Bernard Lipman

(74) *Attorney, Agent, or Firm* — Foley & Lardner, LLP

(57) ABSTRACT

The present invention provides copolymers made up of alkoxyalkyl methacrylate and/or alkoxyalkyl acrylate monomers in combination with one or more additional hydrophobic monomers. The copolymers may be used in the manufacture of intraocular lenses, including both the optic and haptic portions of the lenses. The present invention also provide methods for making intraocular lenses from the copolymers.

17 Claims, 2 Drawing Sheets

MATERIALS FOR MAKING HYDROPHOBIC INTRAOCULAR LENS

CROSS REFERENCES TO RELATED APPLICATIONS

This application is a divisional application of U.S. patent application Ser. No. 10/981,764, filed Nov. 5, 2004, now U.S. Pat. No. 7,067,602, which claims priority to U.S. Provisional Application No. 60/517,107, filed Nov. 5, 2003, and U.S. Provisional Application No. 60/610,195, filed Sep. 16, 2004, the entire disclosures of which are incorporated herein by reference in their entireties and for all purposes as if fully set forth herein.

FIELD OF THE INVENTION

This invention relates to copolymers that include hydrophobic monomers and alkoxyalkyl methacrylate monomers and/or one or more alkoxyalkyl acrylate monomers. The invention also relates to intraocular lenses made from the copolymers, and methods of making such lenses.

BACKGROUND OF THE INVENTION

Various types of intraocular lenses (IOLs) are known. For example, there are known one-piece intraocular lenses and composite intraocular lens having multiple pieces. A one-piece intraocular lens is one where both optic and non-optic portions are made from one material. The non-optic portions of IOLs are referred to as haptic portions, and are used for attachment purposes. Two general designs for the haptics are a "plate-type" and a "C-haptic" type, both of which may have a variety of shapes. A plate design is shown in FIGS. 1A and 1B. A "C" design is shown in FIGS. 2A and 2B. These Figures are discussed in more detail below.

It is desired that the length of incision needed to insert the intraocular lens into the eye be reduced. Reducing the length of the incision requires the use of a very soft material for the lens. The material should be soft enough to permit the lens to be folded, inserted through the incision, and released. Thus, intraocular lenses are preferably foldable so that they can be easily inserted into the eye. Approaches to achieve foldable materials include the use of lenses formed of hydrophobic silicone-polymers, certain hydrophilic 2-HEMA homopolymers, and composites of a hydrophilic optical core with hydrophobic poly(methyl)methacrylate (p-MMA) based haptics.

IOLs with mechanically-attached haptics are lenses where the optic-portion and the haptic-portion are made separately, usually from different materials, and attached. For example, the lens portion can be made of a hydrogel or silicone-based material and the C-shape haptics from a rigid material like p-MMA, polyvinylidene fluoride (PVDF), and polysulfones. The p-MMA haptics are attached to holes drilled into the optic portion.

Although P-MMA is the traditional hydrophobic intraocular lens it is not easily foldable and requires a relatively large incision for insertion. To make hydrophobic materials foldable, rubber-like materials, such as silicone derivatives, have been included in the rigid polymer matrix or materials consisting primarily of silicone derivatives have been used. Although the softness of a primarily silicone material is ideal for folding prior to insertion, when the lens and its haptics unfold in the eye, the almost gel-like softness of the lens makes it difficult for a surgeon to properly position the lens in the eye. Furthermore, the silicone lens often does not provide sufficient rigidity for the lens after insertion and the combination of deformation from compressive forces along with lens movement can produce lens distortion and compromise the optical integrity of the lens.

Because of its inherent properties, p-hydroxyethyl methacrylate (a homopolymer of HEMA) has been used as a foldable material for intraocular lenses. However, the low refractive index of p-HEMA when hydrated leads to limitations in the optical center design and a compromise between its folding ability and its optical requirements.

One of the limitations of one-piece P-HEMA hydrogel lenses has been that the haptic portion lacks the desired modulus and can compromise lens positioning. To address this issue, polymer materials have been combined to give a soft, foldable intraocular composite lens such as P-HEMA or other soft acrylic material for the optic zone, and a rigid structure around the outside of the lens, made from a hard plastic such as P-MMA. See U.S. Pat. No. 4,718,906 and U.S. Pat. No. 5,326,506, both hereby incorporated by reference in their entireties, which describe composite intraocular lenses. These multicomponent materials are made by embedding one material in the other, by concurrent extrusion processes, by solidifying the hard material about the soft material, or by forming an interpenetrating network of the rigid component into a preformed hydrophilic core.

U.S. Pat. No. 5,326,506, discloses a composite intraocular lens including a soft, pliable inner lens optic using rigid haptics. The lens optic material is a low water content material such as a copolymer of 2-HEMA and hydroxy hexyl-methacrylate which has a high refractive index due to its low water content. The hard, yet foldable, P-MMA haptics, are attached by an interpenetrating network.

U.S. Pat. No. 4,764,169, hereby incorporated by reference in its entirety, discloses a composite intraocular lens including a small, hard inner lens optic and a soft, pliable skirt surrounding the lens optic. The lens optic material is a relatively hard material such as P-MMA, polysulfone, or polycarbonate. The soft, pliable skirt is a silicone, hydrogel, or like material.

SUMMARY OF THE INVENTION

The invention provides copolymers, intraocular lenses, blanks for intraocular lenses, and methods for making intraocular lenses.

One embodiment of the present invention provides a copolymer made up of monomeric subunits that include:

(a) one or more hydrophobic monomers, which can be the same or different; and (b) one or more alkoxyalkyl methacrylate monomers, which can be the same or different, and/or one or more alkoxyalkyl acrylate monomers, which can be the same or different. In the copolymers, the primary monomeric subunits of the copolymer by weight are the combination of the one or more alkoxyalkyl methacrylate and/or the one or more alkoxyalkyl acrylate monomers. As used herein primary or primarily means that component(s) recited in relation thereto, for example, the one or more alkoxyalkyl methacrylate monomers in combination with the alkoxyalkyl acrylate monomers, has the highest percentage of all individual monomers present in the copolymer. In some embodiments, the one or more alkoxyalkyl methacrylate monomers and/or the alkoxyalkyl acrylate monomers will make up a majority, i.e. greater than 50 percent, of the copolymer measured by weight. In the present compositions, generally the one or more hydrophobic monomers combined with the one or more alkoxyalkyl methacrylate and/or the one or more alkoxyalkyl acrylate monomers will make up the majority, for example 75, 80, 85, 90, 95, 97 percent or more, of the copolymer by weight.

In some of the copolymers, the one or more hydrophobic monomers are selected from acrylate monomers, methacrylate monomers, or combinations thereof. For example, the one or more hydrophobic monomers can be selected from alkoxyalkoxyalkyl acrylate monomers, alkoxyalkoxyalkyl methacrylate monomers, or combinations thereof. In some copolymers, the one or more hydrophobic monomers are selected from alkyl methacrylate monomers, ethoxyethoxyethyl methacrylate monomers, ethoxyethoxyethyl acrylate monomers, or combinations thereof. When alkyl methacrylate monomers are present, they can be selected from $C_1$ alkyl to $C_{15}$ alkyl methacrylate monomers and in some embodiments are selected from methyl methacrylate monomers, ethyl methacrylate monomers, propyl methacrylate monomers, butyl methacrylate monomers, hexyl methacrylate monomers, lauryl methacrylate monomers, or combinations thereof. In some embodiments, at least one of the one or more hydrophobic monomers is butyl methacrylate. In still other embodiments, at least one of the one or more hydrophobic monomers is methyl methacrylate.

In certain copolymers, the one or more alkoxyalkyl methacrylate monomers and/or alkoxyalkyl acrylate monomers are about 45 to about 99 percent of the copolymer by weight and the one or more hydrophobic monomers are about 1 to about 55 percent of the copolymer by weight. The one or more alkoxyalkyl methacrylate monomers and/or alkoxyalkyl acrylate monomers can also make up a majority of the copolymer by weight. In some embodiments, the one or more alkoxyalkyl methacrylate monomers and/or alkoxyalkyl acrylate monomers are about 85 to about 97 percent of the copolymer by weight and the one or more hydrophobic monomers are about 3 to about 15 percent of the copolymer by weight. In some of the present copolymers, at least one of the one or more alkoxyalkyl methacrylate monomers is ethoxyethyl methacrylate and the one or more hydrophobic monomers is ethoxyethoxyethyl acrylate.

The present copolymers can also include one or more ultraviolet absorbing compounds, one or more crosslinking agents, or combinations thereof. Any crosslinking agent known in the art may be used in conjunction with the invention. As such, the copolymer can include crosslinkers such as, but not limited to, incorporated ethylene glycol dimethacrylate, incorporated tetraethylene glycol dimethacrylate, and/or incorporated trimethylol propane trimethacrylate. Further copolymers include at least one alkoxyalkyl methacrylate monomer and at least one alkoxyalkyl acrylate monomer.

The present copolymers can have glass transition temperatures below about 25° C., for example from about −25° C. to about 25° C., from about −5° C. to about 15° C., or about 0° C. to about 5° C. The present copolymers can also have a refractive index of greater than about 1.40 or about 1.40. For example, in some embodiments the refractive index is 1.48, or higher. In some embodiments, the copolymers contain substantially no aromatic polymer. In some of the present copolymers, the equilibrium water content of the copolymer is less than 5 percent or less than about 5 percent, for example less than 2.5 percent or less than about 2.5 percent.

In some embodiments, a lens formed from the copolymer and having a central thickness of up to 1 mm unfolds in less than or about 2 minutes when placed in a saline solution at a temperature of 36° C. or about 36° C. In some such embodiments, the lens unfolds in less than or about 1 minute and in other embodiments unfolds in less than or about 30 seconds under the conditions specified. In some embodiments, a lens formed from the copolymer does not develop bubbles or voids when placed in a saline solution for 12 hours to 48 hours at a temperature of 40° C. or about 40° C. after cooling to room temperature. In other words, these materials show now glistening after soaking for these periods of time and cooling.

The present invention also provides an intraocular lens that includes an optic portion made of any one of the described copolymers. The intraocular lens also includes one or more haptic portions. The optic portion and the one or more haptic portions can be made of the same copolymer, such as in a one piece intraocular lens, or different materials, such as with a multiple piece intraocular lens. Some intraocular lenses can further include a polymer surrounding the copolymer such that the polymer is not the same as the copolymer and the copolymer forms a core of the optic portion. The present copolymers can also take the form of a blank for an intraocular lens.

The present invention also provides methods for making an intraocular lens. Some methods include forming an intraocular lens from any of the described copolymers. Some of the described methods include:
(a) polymerizing a mixture including:
  (i) one or more hydrophobic monomers which can be the same or different; and
  (ii) one or more alkoxyalkyl methacrylate monomers which can be the same or different and/or one or more alkoxyalkyl acrylate monomers which can be the same or different, to form a copolymer, in which the primary component of the copolymer by weight is the one or more alkoxyalkyl methacrylate and/or the one or more alkoxyalkyl acrylate monomers; and
(b) forming an optic portion from the copolymer.

In some embodiments of these methods, the one or more hydrophobic monomers can be selected from acrylate monomers, methacrylate monomers or combinations thereof. In these and other methods the one or more hydrophobic monomers can be selected from alkoxyalkoxyalkyl acrylate monomers, alkoxyalkoxyalkyl methacrylate monomers, or combinations thereof. In some methods, the one or more hydrophobic monomers can be selected from ethoxyethoxyethyl acrylate, lauryl methacrylate, methyl methacrylate, or combinations thereof.

In some methods, the mixture can include the one or more hydrophobic monomers in an amount of about 1 to about 49 percent of the copolymer by weight and the one or more alkoxyalkyl methacrylate monomers and/or alkoxyalkyl acrylate monomers in an amount of about 50 to about 99 percent of the copolymer by weight. In certain methods, the combination of the one or more alkoxyalkyl methacrylate monomers and/or alkoxyalkyl acrylate monomers comprise a majority of the mixture by weight. In certain methods, the one or more hydrophobic monomers are about 3 to about 15 percent of the mixture by weight and the one or more alkoxyalkyl methacrylate monomers and/or alkoxyalkyl acrylate monomers together are about 85 to about 97 percent of the mixture by weight.

In some embodiments of the described methods, at least one of the one or more alkoxyalkyl methacrylate monomers is ethoxyethyl methacrylate and the one or more hydrophobic monomers is ethoxyethoxyethyl acrylate. The mixtures used to make the intraocular lens can also include one or more ultraviolet absorbing compounds, one or more crosslinking agents, one or more initiators, or combinations thereof. In certain embodiments, neither the mixture nor the copolymer contain substantially any aromatic polymer and in some embodiments no aromatic monomer is present in the polymerization mixture.

The present methods can also include (c) forming a polymer around the copolymer such that the polymer is not the same as the copolymer and the copolymer forms a core of the optic portion. Forming a polymer around the copolymer can occur by polymerizing the polymer around the copolymer. The present methods can also include forming an intraocular lens blank from the copolymer, such that (b) comprises forming the optic portion from the intraocular lens blank. In these methods (b) can also include cutting, milling or both cutting and milling the intraocular lens blank into the optic portion.

In the present methods, (a) and (b) can occur simultaneously or (b) can occur subsequent to (a). The present methods can also include (d) forming one or more haptic portions from the copolymer and/or (e) attaching one or more haptic portions to the optic portion.

The present invention also provides a method for modifying, correcting or improving an individual's eyesight that includes inserting any of the present intraocular lenses into an eye of a subject. This method can also include folding the intraocular lens prior to inserting the intraocular lens into the eye and allowing the intraocular lens to unfold after it is inserted into the eye. These methods can also include removing a lens, either natural or artificial, from the eye of the subject prior to inserting the intraocular lens.

Further objects, features, and advantages of the present invention will become apparent from the detailed description of preferred embodiments that follows.

DETAILED DESCRIPTION OF THE PREFERRED EMBODIMENTS

Figure 1A:
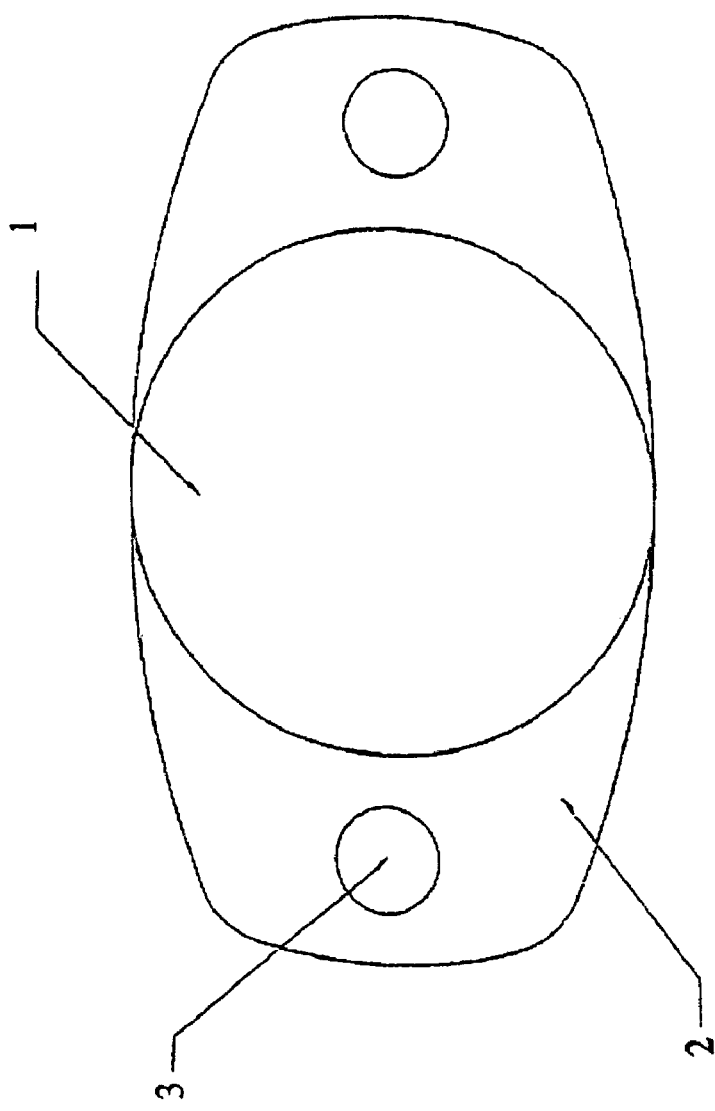
FIG. 1A is a top view of an intraocular lens having a plate-shaped haptic.

The present invention provides hydrophobic copolymer compositions that are particularly useful for intraocular lenses. A copolymer for the purposes of the present invention means a polymer formed from 2 or more different polymerizable monomers. These copolymers have as their primary components, i.e. the primary monomer present in the copolymer by weight, a combination of one or more alkoxyalkyl methacrylate monomers and/or one or more alkoxyalkyl acrylate monomers. For purposes of the present invention, all of the one or more alkoxyalkyl methacrylate monomers, which can be the same or different, and/or the one or more alkoxyalkyl acrylate monomers, which can also be the same or different, are considered as single component of the present copolymers.

Alkoxyalkyl methacrylate monomers can be represented by the formula $R_1OR_2MA$ where $R_1$ and $R_2$ are alkyl groups and MA is methacrylate. Alkoxyalkyl acrylate monomers can be represented by the formula $R_3OR_4Ac$ where $R_3$ and $R_4$ are alkyl groups and Ac is acrylate. In some embodiments, $R_1$ to $R_4$ can be independently selected from alkyl groups having 1 to 8 carbon atoms and in some embodiments 1, 2, 3, 4, 5 or 6 carbon atoms. Alkyl groups that can be used include straight chain alkyl groups, including but not limited to methyl, ethyl, propyl, butyl, pentyl, hexyl, heptyl, and octyl groups. Alkyl groups can also include branched chain isomers of straight chain alkyl groups including but not limited to the following, which are provided by way of example only: $-CH(CH_3)_2$, $-CH(CH_3)(CH_2CH_3)$, $-CH(CH_2CH_3)_2$, $-C(CH_3)_3$, $-C(CH_2CH_3)_3$, $-CH_2CH(CH_3)_2$, $-CH_2CH(CH_3)$ $(CH_2CH_3)$, $-CH_2CH(CH_2CH_3)_2$, $-CH_2C(CH_3)_3$, $-CH_2C(CH_2CH_3)_3$, $-CH(CH_3)CH(CH_3)(CH_2CH_3)$, $-CH_2CH_2CH(CH_3)_2$, $-CH_2CH_2CH(CH_3)(CH_2CH_3)$, $-CH_2CH_2CH(CH_2CH_3)_2$, $-CH_2CH_2C(CH_3)_3$, $-CH(CH_3)CH_2CH(CH_3)_2$, $-CH(CH_3)CH(CH_3)CH(CH_3)_2$, $-CH_2CH_2CH_2C(CH_3)_3$, $-CH_2CH_2CH_2CH(CH_3)_2$, $-CH_2CH_2CH(CH_3)C(CH_3)_3$, $-CH_2CH_2CH(CH_3)CH$ $(CH_3)_2$, and the like.

The present copolymers also include one or more hydrophobic monomers other than the aforementioned one or more alkoxyalkyl methacrylate monomers and/or the one or more alkoxyalkyl acrylate monomers. When more than one hydrophobic monomer is used, each individual monomer is considered to be a single component of the copolymer. Accordingly, each individual monomer present in the copolymer other than either the one or more alkoxyalkyl methacrylate monomers or the one or more alkoxyalkyl acrylate monomers will make up less of the copolymer by weight than the combined weight of the one or more alkoxyalkyl methacrylate monomers and the one or more alkoxyalkyl acrylate monomers. As will be apparent to the skilled artisan, the other monomers present in the copolymer, such as the hydrophobic monomers, can cumulatively, but not separately, weigh more than the aforementioned one or more alkoxyalkyl methacrylate monomers combined with the one or more alkoxyalkyl acrylate monomers.

As used herein, primary or primarily means that a component recited in relation thereto, for example, the one or more alkoxyalkyl methacrylate monomers in combination with the alkoxyalkyl acrylate monomers, has the highest percentage of all individual monomers present in the copolymer. In some embodiments, the one or more alkoxyalkyl methacrylate monomers and/or the alkoxyalkyl acrylate monomers will make up a majority, i.e. greater than 50 percent, of the copolymer measured by weight in which case the one or more hydrophobic polymers can make up about 1 to 49 percent of the copolymer. The one or more alkoxyalkyl methacrylate monomers and/or the alkoxyalkyl acrylate monomers can make up about 45 to 99 percent, for example from about 85 to 95 percent, from 50 to 99 percent, from 85 to 97 percent, from 80 to 97 percent, from 70 to 97 percent, or from 65 to 97 percent, of the copolymer by weight. The present copolymers can include at least one alkoxyalkyl methacrylate monomer and at least one alkoxyalkyl acrylate monomer. All percentages discussed herein are by weight unless otherwise specified.

As used herein, the term "copolymer" refers to a polymer that is formed from at least two different monomers. The term "copolymer" thus includes terpolymers and any polymer that is formed from at least two different monomers and may be formed from two, three, four, or more different monomers.

In some of the copolymers, the one or more alkoxyalkyl methacrylate monomers and/or the alkoxyalkyl acrylate monomers can partially or wholly be made up of ethoxyethyl methacrylate or ethoxyethyl acrylate.

In the present copolymers, the identity of the one or more hydrophobic monomers is not particularly limited, although such hydrophobic monomers will generally not include an aromatic constituent. In some of the present copolymers, the hydrophobic monomers can be acrylate monomers, methacrylate monomers and combinations thereof. Other suitable hydrophobic monomers include alkoxyalkoxyalkyl acrylate monomers, alkoxyalkoxyalkyl methacrylate monomers, and combinations thereof. Specific hydrophobic monomers can be alkyl methacrylate monomers, ethoxyethoxyethyl methacrylate monomers, ethoxyethoxyethyl acrylate monomers and combinations thereof with specific examples of alkyl methacrylate monomers being $C_1$ alkyl to $C_{15}$ alkyl methacrylate monomers such as, but not limited to, methyl methacrylate monomers, ethyl methacrylate monomers, propyl methacrylate monomers, butyl methacrylate monomers, hexyl methacrylate monomers, lauryl methacrylate monomers, and combinations thereof. Generally, the hydrophobic-monomers will make up about 1 to about 55, and in some embodiments from about 1 to about 53 percent of the copolymer by weight, including any percentage falling within this range.

In the present copolymers, generally the one or more hydrophobic monomers combined with the one or more alkoxyalkyl methacrylate and/or the one or more alkoxyalkyl acrylate monomers will make up the great majority, for example 75, 80, 85, 90, 95, 97 percent or more, of the copolymer.

The present copolymers can also include various other components that improve the characteristics of the copolymer. Non-limiting examples of other components include one or more ultraviolet absorbing compounds, one or more crosslinking agents, such as, but not limited to, incorporated ethylene glycol dimethacrylate, incorporated tetraethylene glycol dimethacrylate, incorporated trimethylol propane trimethacrylate, one or more colorants, and combinations thereof. Those skilled in the art will recognize that various known cross-linking agents may be used in the copolymers and methods in accordance with the invention.

When a copolymer is said to include a monomer such as ethoxyethyl methacrylate, it will be understood that this means that the ethoxyethyl methacrylate monomer has been reacted and incorporated into the copolymer.

One exemplary composition contains about 93.5 percent to about 94.5 percent of ethoxyethyl methacrylate and about 4.75 to about 5 percent ethoxyethoxyethyl acrylate, with the balance of the copolymer being made up of other components, such as UV absorbers, initiation agents and/or crosslinking agents. Another exemplary composition contains about 88.5 percent to about 89.5 percent, for example about 90 percent, of ethoxyethyl methacrylate and about 9.75 to about 10 percent, for example about 9.9 percent, ethoxyethoxyethyl acrylate with the balance of the copolymer again being made up of other components. Another specific composition contains a lower amount of ethoxyethyl methacrylate, about 46 to about 47.5 percent, and a higher amount of a combination of hydrophobic monomers, specifically about 37.5 percent to about 38 percent lauryl methacrylate and about 14.75 to about 15 percent methyl methacrylate, again with the balance of the copolymer being made up of UV absorbers, initiation agents and/or crosslinking agents. As can be seen from these exemplary compositions, the present intraocular lens can have a range of material components and still have the desired characteristics.

In most embodiments, the present copolymers will contain no, or substantially no, monomers that have aromatic constituents. Previously, aromatic monomers have been added to polymers in order to increase the refractive index of the polymer so as to make the polymer more suitable for lens formation. However, aromatic monomers also increase the stiffness of the resulting polymer making any resulting lens made from the polymer more difficult to manipulate or fold without damaging the lens. The present copolymers overcome this problem by balancing the physical characteristics of the copolymer used to make the lens. Accordingly, in some embodiments 10 percent, 5 percent, 2 percent, 1 percent, 0.1 percent or less of the monomers used to make the present copolymers will have aromatic constituents.

The present copolymers can be designed to have a wide range of physical characteristics. In some instances, the present copolymers can be designed to have glass transition temperatures below at or about 25° C., such as from at or about −25° C. to at or about 25° C., from about −5° C. to about 15° C., or from at or about 0° C. to at or about 5° C. One skilled in the art will recognize that the lower the glass transition temperature the more rubbery the copolymer. As the present copolymers have been designed to be used as intraocular lenses, they also typically have a high refractive index, which is generally above about 1.40. Some of the present copolymers can have a refractive index of 1.48 or higher. Because the present copolymers are hydrophobic, they can also have equilibrium water contents that are about 5 percent or less, for example 3 percent, 2 percent, 1 percent or less. Due to their low water contents, the present copolymers are generally not considered hydrogels. Generally, the present lenses also have advantageous properties compared to prior lenses because they have a higher refractive index compared to lenses containing silicone or p-hydroxyethyl methacrylate and are more flexible, e.g., foldable, than hydrophobic lenses that include aromatic monomers to increase the refractive index of the resulting polymer.

The present invention also provides intraocular lenses made at least partially from the present copolymers. Such intraocular lenses include an optic portion and one or more haptic portions. Typically, the present copolymers will make up part or all of the optic portion of the intraocular lens. In some embodiments, the optic portion of the lens will have a core made from one of the present copolymers surrounded by different polymer or material. Lenses in which the optic portion is made up of at least partially of one of the present copolymers will usually also have a haptic portion. The haptic portion can also be made of copolymer or can be made of a different material, for example another polymer.

In some embodiments, the present intraocular lens is a one-piece lens having a soft, foldable central optic region and an outer peripheral region (haptic-region) in which both regions are made of the same copolymer. In other embodiments, the optic and haptic regions can be formed from different types of polymers or materials, if desired. Some lenses can also have haptic portions that are made up of different materials, for example where one or more haptic portions is made from the same material as the optic portion and other haptic portions are made of materials other than the copolymer. Multicomponent lenses can be made by embedding one material in the other, concurrent extrusion processes, solidifying the hard material about the soft material, or forming an interpenetrating network of the rigid component into a preformed hydrophobic core. In instances where one or more haptic portions are made from a different material than the optic portion of the lens, the haptic portion can be attached to the optic portion in any manner known in the art, such as by drilling a hole or holes in the optic portion and inserting the haptic portion.

The present copolymers have been designed so that they are capable of being folded so that the intraocular lens can be inserted into the eye of an individual through a small incision. The haptic portion of the lens provides the required support for the lens in the eye after insertion and unfolding of the lens and tends to help stabilize the position of the lens after insertion and the closure of the incision. The shape of the haptic portion design is not particularly limited and can be any desired configuration, for example, either a plate type or graduated thickness spiral filaments, also known as a C-loop design.

Figure 1B:
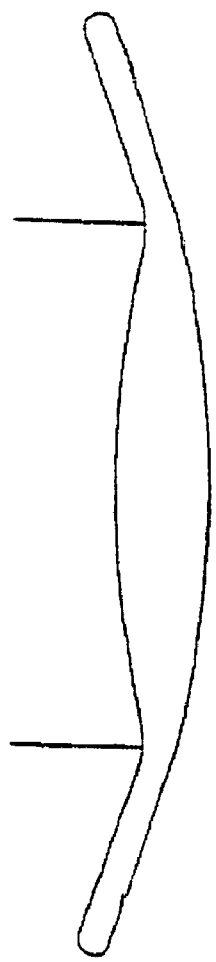
FIG. 1B is a side view of the intraocular lens having a plate-shaped haptic shown in FIG. 1A.
Figures 2A, 2B:
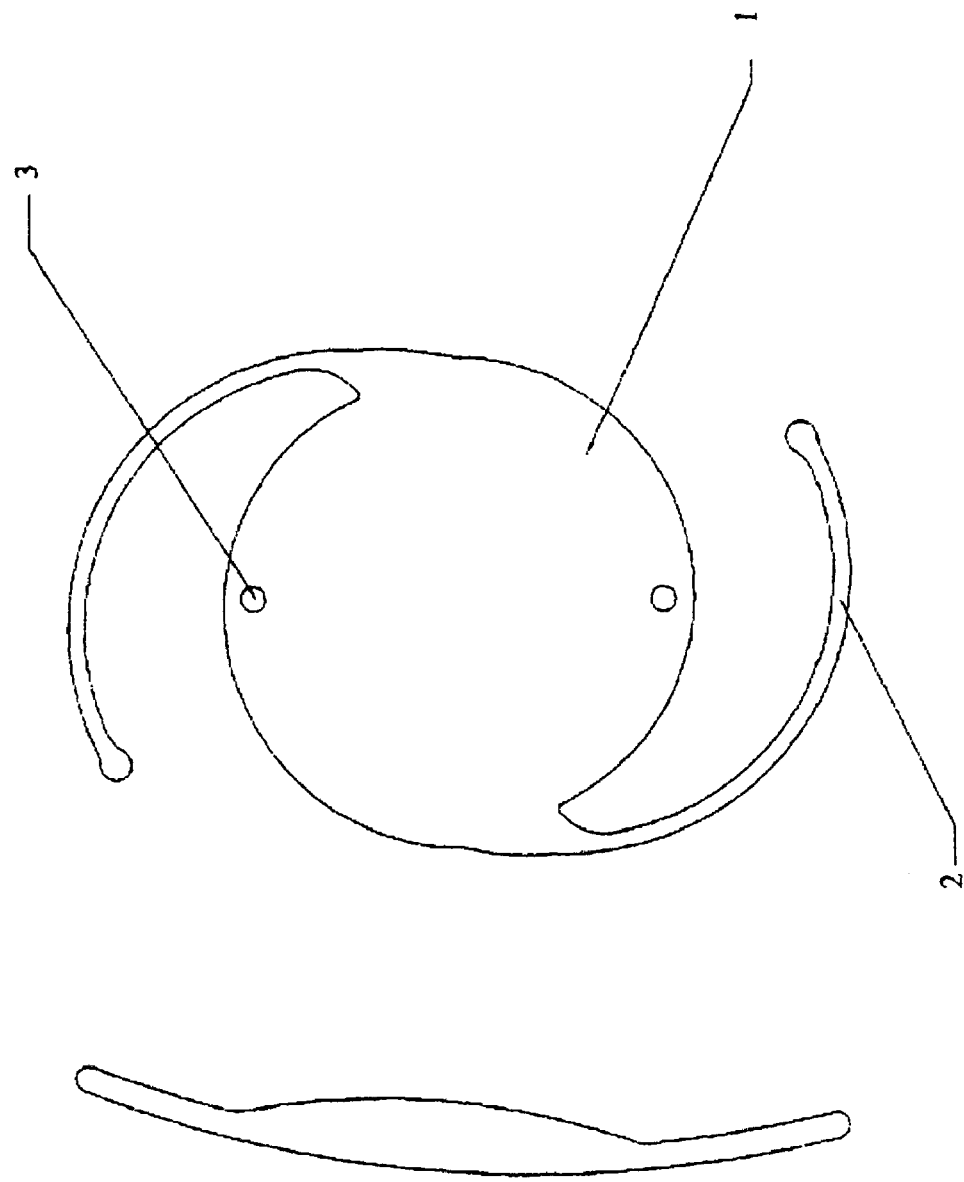
FIG. 2A is a top view of an intraocular lens having a C-shaped haptic.
FIG. 2B is a side view of the intraocular lens having a C-shaped haptic shown in FIG. 2A.

FIGS. 1A, 1B, 2A, and 2B illustrate examples of intraocular lenses in accordance with the present invention. The figures are for illustrative purposes only and do not limit the scope of the invention. For instance, the intraocular lens can be any type of intraocular lens. In the figures, 1 is the optic portion of the lens, 2 is the haptic portion, and 3 is a positioning hole. One skilled in the art of intraocular lenses understands the functions of these portions of the intraocular lens.

The optic portion 1 can be approximately 6 mm in diameter prior to hydration. The 6 mm diameter is fairly standard in the art, and is generally chosen to cover the pupil in its fully dilated state under naturally occurring conditions. However, other sizes are possible and the present invention is not limited to any particular diameter or size of intraocular lens. Furthermore, it is not necessary that the lens optic portion be circular; it could also be oval, square, or any other shape as desired.

The intraocular lens can further include one or more non-optical haptic components 2 extending away from the outermost peripheral surface of the optic portion. The haptic components can be of any desired shape, for example, graduated spiral filaments or flat plate sections and are used to support the lens within the posterior chamber of the eye. Lenses having any desired design configuration can be fabricated. Further, although two types of haptic designs are shown in the figures, the haptics can have configurations other than those illustrated. Should the intraocular lens include other components besides the optical and haptic portions, such other portions can be made of a copolymer as are the haptic and optic portions, or if desired, another material.

The intraocular lenses of the invention may be inserted into the eye in known manners. For example, the intraocular lens may be folded prior to insertion into the eye by small, thin forceps of the type typically used by ophthalmic surgeons. After the lens is in the targeted location, it is released to unfold. As is well known in the art, typically the lens that is to be replaced is removed prior to insertion of the intraocular lens. The intraocular lens of the present invention can be made of a generally physiologically inert soft polymeric material that is capable of providing a clear, transparent, refractive lens body even after folding and unfolding. In some embodiments, the foldable intraocular lens of the present invention can be inserted into any eye by injection whereby the mechanically compliant material is folded and forced through a small tube such as a 1 mm to 3 mm inner diameter tube.

The copolymers can be prepared using conventional polymerization techniques known to those in the field of polymer chemistry. Crosslinkers may be employed in the polymerization reaction. For example, any crosslinking or difunctional monomer, can be used in effective amounts to give the desired crosslinking density. For example, in a concentration range of 0 to about 10 percent, such as about 0.01 to about 4 percent, or in some embodiments from 0.5 to 3 percent by weight, based on the weight of the polymer. Examples of suitable crosslinking agents include di-olefinic functional component or ethylene glycol dimethacrylate (EGDMA). Generally, crosslinkers help to enhance the resulting copolymer's dimensional stability.

Also, if desired an initiator can be used in the polymerization. Any initiator commonly used in the art, such as azo derivatives, like 2,2-azobis (2,4-dimethylvaleronitrile) and propanenitrile,2-methyl,2,2'-azobis, can be used. The initiator is used in an amount effective for initiation purposes, and is generally present from about 0.01 to 1.0 percent by weight, based on the weight of the copolymer.

The copolymer used in the present invention can also include additional monomers, such as monomers that impart UV absorption to the copolymer. UV absorbing monomers are typically aromatic compounds with olefinic functionality. The advantageous ultraviolet (UV) absorbing compounds can be added prior to polymerization for incorporation into the resultant polymer, as is well known in the art. The UV absorber should preferably be capable of polymerization into the lens matrix so as to be stable under physiologic conditions. Any monomer copolymerizable with the described monomers can optionally be used, so long as such does not materially, adversely effect the basic characteristics of the intraocular lens. Examples of useful additional monomers that can used are described in U.S. Pat. No. 5,326,506, hereby incorporated by reference, directed to a composite intraocular lens. Such optional additional monomers, preferably are present in a total amount of not more than 10 weight percent, generally less than 5 weight percent, based on the total weight of the copolymer.

As described above, it may be useful to add crosslinking agents such as ethylene glycol dimethacrylate (EGDMA) or trimethylol propane trimethacrylate (TMPTA), for example, to enhance the resulting copolymer's dimensional stability. It may also be advantageous to add ultraviolet (UV) absorbing compounds with the lens monomers prior to polymerization for incorporation into the resultant polymer. The UV absorber should preferably be capable of polymerization into the lens matrix so as to resist extraction under physiologic conditions. The UV-absorbing monomer can be present in an amount effective to give the desired UV-absorbing properties, generally less than 4 percent by weight of the copolymer, such as from 0.01 to about 1 percent by weight of the copolymer.

Examples of specific copolymers useful in the present invention are shown below in Table 1 which are also discussed in the examples where all weights are shown in grams.

TABLE 1

| Examples | EOEMA | EEEA | LME | MMA | TMPTA | EGDMA |
|---|---|---|---|---|---|---|
| 1 | 125 | 25 | | | 2.506 | 0.656 |
|  | 94.34% | 4.97% | | | 0.50% | 0.13% |
| 2 | 141.1 | | 114.1 | 45 | 1.51 | 0.3975 |
|  | 46.67% | | 37.74% | 14.88% | 0.50% | 0.13% |
| 3 | 224.9 | 25 | | | 1.8942 | 0.4836 |
|  | 89.08% | 9.90% | | | 0.75% | 0.19% |
| 4 | 224.8 | 25.1 | | | 2.5038 | 0.1811 |
|  | 88.94% | 9.93% | | | 0.99% | 0.07% |
| 5 | 475 | 25 | | | 5 | 1.3 |
|  | 93.75% | 4.93% | | | 0.99% | 0.26% |
| 6 | 712.5 | 37.5 | | | 3.75 | 3.75 |
|  | 93.99% | 4.95% | | | 0.49% | 0.49% |

Other examples of specific copolymers useful in the present invention are shown below in Table 2 where all amounts are shown in weight percents where the total weight of the monomers adds up to 100% and the amounts of the cross-linkers and initiators is based on the total weight of the monomers. These copolymers are formed using the same procedures disclosed in Examples 1-6. 2,2-Azobis (2,4-dimethylvaleronitrile) was used as an initiator to prepare the copolymers of each of Examples 1-33 in an amount of about 0.07 weight percent based on the total weight of the monomers.

from 0.793 mm to 0.999 mm. In some embodiments, the lenses unfold in times of less than 1 minute and in still other embodiments, they unfold in less than or about 30 seconds.

The copolymers used in the intraocular lenses preferably have a refractive index (RI) of greater than or about 1.4 generally from about 1.4 to about 1.5. An advantage of copolymers of the present invention is that they can be folded prior to insertion, thereby reducing the size of the incision. Generally, the RI value for a hydrogel decreases progressively with increasing water content. The RI value of a material influences the design and the parameters of an intraocular

TABLE 2

| Example | EOEMA | EEEA | MMA | LME | BMA | EGDMA | TMPTA | Initiator | $T_g$ |
|---|---|---|---|---|---|---|---|---|---|
| 7  | 85   | 0   | 7.5  | 7.5 | 0  | 0.2 | 1    | 0.07 | —    |
| 8  | 85   | 0   | 7.5  | 7.5 | 0  | 0   | 1.3  | 0.07 | —    |
| 9  | 85   | 0   | 7.5  | 7.5 | 0  | 0.4 | 1    | 0.07 | —    |
| 10 | 85   | 0   | 7.5  | 7.5 | 0  | 0   | 1    | 0.07 | 10   |
| 11 | 85   | 0   | 5    | 10  | 0  | 0   | 1    | 0.07 | 6    |
| 12 | 85   | 0   | 6    | 9   | 0  | 0   | 1    | 0.07 | 1.2  |
| 13 | 95   | 0   | 5    | 0   | 0  | 0   | 1    | 0.07 | -2.5 |
| 14 | 97   | 0   | 3    | 0   | 0  | 0   | 1    | 0.07 | -0.2 |
| 15 | 85   | 0   | 7.5  | 7.5 | 0  | 0.5 | 1    | 0.07 | —    |
| 16 | 85   | 0   | 7.5  | 7.5 | 0  | 0.5 | 1    | 0.07 | 11/21|
| 17 | 70   | 0   | 0    | 0   | 30 | 0.5 | 1    | 0.07 | —    |
| 18 | 65   | 0   | 5    | 0   | 30 | 0.5 | 1    | 0.07 | 24   |
| 19 | 86.5 | 0   | 10   | 3.5 | 0  | 0.5 | 1    | 0.07 | —    |
| 20 | 85   | 0   | 10   | 5   | 0  | 0.5 | 1    | 0.07 | 16   |
| 21 | 85   | 0   | 10   | 0   | 5  | 0.5 | 1    | 0.07 | —    |
| 22 | 80   | 0   | 10   | 0   | 10 | 0.5 | 1    | 0.07 | —    |
| 23 | 70   | 0   | 10   | 0   | 20 | 0.5 | 1    | 0.07 | 26   |
| 24 | 87.5 | 0   | 10   | 2.5 | 0  | 0.5 | 1    | 0.07 | —    |
| 25 | 85   | 0   | 12.5 | 2.5 | 0  | 0.5 | 1    | 0.07 | 16   |
| 26 | 82.5 | 0   | 15   | 2.5 | 0  | 0.5 | 1    | 0.07 | —    |
| 27 | 90   | 0   | 10   | 0   | 0  | 0.5 | 1    | 0.07 | —    |
| 28 | 87.5 | 2.5 | 10   | 0   | 0  | 0.5 | 1    | 0.07 | 13   |
| 29 | 90   | 0   | 10   | 0   | 0  | 0.5 | 1    | 0.07 | 19   |
| 30 | 95   | 0   | 5    | 0   | 0  | 0.5 | 1    | 0.07 | 11   |
| 31 | 95   | 5   | 0    | 0   | 0  | 0.5 | 1    | 0.07 | 4    |
| 32 | 90   | 5   | 5    | 0   | 0  | 0.7 | 1    | 0.07 | 1    |
| 33 | 85   | 5   | 10   | 0   | 0  | 0.7 | 0.75 | 0.07 | 15   |

Unfolding was measured at 36° C. for each of examples 7, 8, 9, 10, and 16 in Table 2. Examples 7, 8, 9, 10 each unfolded at times of less than 30 seconds, and Example 16 unfolded at a time of less than 1 minute and 30 seconds. The CT (central thickness) for lenses formed from the copolymers of Examples 7, 8, 9, 10, and 16 were respectively 0.975 mm, 0.982 mm, 0.999 mm, 0.793 mm, and 0.937 mm. The thickness of haptics formed from the copolymer of each of Examples 7, 8, and 9 were respectively 0.29 mm, 0.29 mm, and 0.28 mm. The refractive index at 22° C. for the copolymers of Examples 7 and 8 were respectively 1.4845 and 1.4840. The refractive index at 35° C. for the copolymers of Examples 7 and 8 were respectively 1.4810 and 1.4815.

Lenses formed from the copolymers described in Tables 1 and 2 do not develop readily observable bubbles or voids in the matrix when such lenses are placed in a saline solution at 40° C. overnight and allowed to cool room temperature. Therefore, no glistening was observed for these lenses. Therefore, in some embodiments, lenses formed from the copolymers of the invention do not form bubbles when placed in a saline solution at 40° C. overnight and then cooled to room temperature.

Lenses formed from the copolymers described in Tables 1 and 2 also have very favorable unfolding properties. For example, lenses formed from the copolymer of Table 2 unfold in less than or about 2 minutes when placed in a saline solution at 37° C. The average thickness of these lenses is generally less than 1 mm such as lenses with a central thickness of lens. Hence, besides biocompatibility, an ideal intraocular lens is foldable and injectable, and has the ability to quickly regain its shape and optical quality after insertion, and has a high RI value. The intraocular lenses of the present invention have been found to possess these desired characteristics. That is, the intraocular lenses of the present invention fulfill the requirements of a high performance intraocular lens and have excellent folding characteristics, a relatively high refraction index, and excellent unfolding characteristics.

The intraocular lenses of the present invention may be formed by methods known in the art. For example, in an exemplary process the monomers that form the copolymer are polymerized into a polymer rod, polymer blanks or discs are formed from the rod, and then the blanks are cut, for example, by a lathe into the intraocular lens. The rods can be made by a procedure which begins with polymerizing, in a mold, such as in a tubular or cylindrical mold, a mixture of initiator and monomers, to form an optically clear soft lens body. As discussed above, it may be desirable to incorporate cross-linking materials and ultraviolet-absorbing compounds during polymerization or into the resultant polymer matrix. In some embodiments the polymer rods are then cut and ground or otherwise machined, into blanks of the desired diameter and thickness by lathe cutting and machine milled at temperatures below the $T_g$ into an intraocular lens.

Generally, the composite material rod is lathe cut or ground to a diameter 0.5 to 2.0 mm thicker than the required distance from the center of the lens body to the furthest edge of the legs or haptics. This rod is then cut into blanks of uniform thickness. The blanks are ground and lapped to a diameter and thickness suitable for lathe cutting and machine milling in the conventional manner into the intraocular lens of the present invention. Because the present polymers can have low glass transition temperatures, the rod or blanks may require cooling below $T_g$ prior to and/or during cutting, lathing and/or milling.

A general description of a stepwise process for forming the blanks into intraocular lenses is set forth in the flow chart below. In the following scheme, the second box in the process should read "Cut first surface of blank," and the sixth box in the process should read, "Cut Second surface of blank." One having ordinary skill in the field of intraocular lens manufacturing, from a review of the present specification, can make intraocular lenses using the general knowledge in the art on intraocular lens manufacture and the process of cryogenic machining.

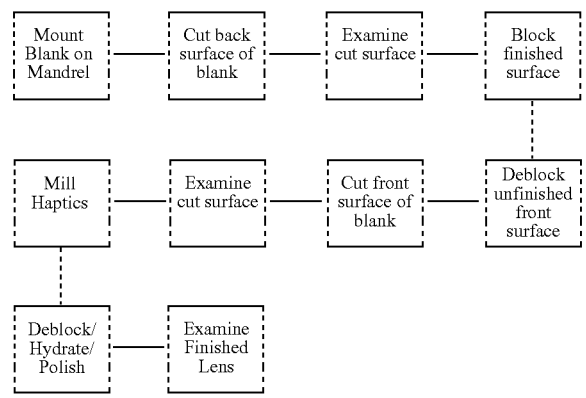

Intraocular lenses can also be made by molding the present copolymer to form all or part of the optic portion of the lens. For example, the present copolymer can be polymerized in a mold by a liquid mixture of monomers and additional components, to form an optically clear soft lens body. These molding methods can involve molding the optics on one half of the lens, such as the anterior or posterior portion, or fully molding the lens. When only half of the optic portion of the lens is formed in the mold then the second side optics can be machined, for example as discussed above. In either of these embodiments, additional material can be molded to allow machining of various haptic designs.

The invention is illustrated by the following non-limiting examples.

EXAMPLES

EOEMA refers to ethoxyethyl methacrylate
EEEA refers to ethoxyethoxyethyl acrylate
TMPTMA and TMPTA refer to trimethylol propane trimethacrylate and trimethylol propane triacrylate respectively
MMA refers to methyl methacrylate
LME refers to lauryl methacrylate
BMA refers to butyl methacrylate
EGDMA refers to ethylene glycol dimethacrylate Example 1

475 grams of ethoxyethyl methacrylate (EOEMA) were mixed with 25 grams of ethoxyethoxyethyl acrylate (EEEA), 2.506 grams of trimethylol propane trimethacrylate (TMPTMA) and 0.656 grams of ethylene glycol dimethacrylate (EGDMA) without solvent. The mixture was degassed while applying vigorous stirring. The mixture was dispensed into cylindrical molds, polymerized at 30° C. for 10 hours, and post-cured at 100° C. for 5 hours. The copolymer was then removed from the molds and formed into blanks. The mechanical formation process comprised cutting the polymer into cylinders of 0.5 to 0.65 inches (1.27 to 1.65 cm.) in diameter and 0.1 to 0.2 inches (0.25 to 0.51 cm.) in thickness. The blanks were further cured at 100° C. for 5 hours. After curing, the blanks were ground to the desired dimensions.

Example 2

141.1 grams of EOEMA were mixed with 114.1 grams of lauryl methacrylate (LME), 45 grams of methyl methacrylate (MME), 1.51 grams of TMPTMA and 0.3975 grams of ethylene glycol dimethacrylate (EGDMA). The mixture was degassed while applying vigorous stirring. The mixture was dispensed into cylindrical molds, polymerized at 30° C. for 10 hours, and post-cured at 100° C. for 5 hours. The copolymer was then removed from the molds and formed into blanks. The mechanical formation process comprised cutting the polymer into cylinders of 0.5 to 0.65 inches (1.27 to 1.65 cm.) in diameter and 0.1 to 0.2 inches (0.25 to 0.51 cm.) in thickness. The blanks were further cured at 100° C. for 5 hours. After curing, the blanks were ground to the desired dimensions.

Example 3

224.9 grams of EOEMA were mixed with 25 grams of EEEA, 1.8942 grams of TMPTMA and 0.4836 grams of ethylene glycol dimethacrylate (EGDMA). The mixture was degassed while applying vigorous stirring. The mixture was dispensed into cylindrical molds, polymerized at 30° C. for 10 hours, and post-cured at 100° C. for 5 hours. The copolymer was then removed from the molds and formed into blanks. The mechanical formation process comprised cutting the polymer into cylinders of 0.5 to 0.65 inches (1.27 to 1.65 cm.) in diameter and 0.1 to 0.2 inches (0.25 to 0.51 cm.) in thickness. The blanks were further cured at 100° C. for 5 hours. After curing, the blanks were ground to the desired dimensions.

Example 4

224.8 grams of EOEMA were mixed with 25.1 grams of EEEA, 2.5038 grams of TMPTMA and 0.1811 grams of ethylene glycol dimethacrylate (EGDMA). The mixture was degassed while applying vigorous stirring. The mixture was dispensed into cylindrical molds, polymerized at 30° C. for 10 hours, and post-cured at 100° C. for 5 hours. The copolymer was then removed from the molds and formed into blanks. The mechanical formation process comprised cutting the polymer into cylinders of 0.5 to 0.65 inches (1.27 to 1.65 cm.) in diameter and 0.1 to 0.2 inches (0.25 to 0.51 cm.) in thickness. The blanks were further cured at 100° C. for 5 hours. After curing, the blanks were ground to the desired dimensions.

Example 5

475 grams of EOEMA were mixed with 25 grams of EEEA, 5 grams of TMPTMA and 1.3 grams of ethylene glycol dimethacrylate (EGDMA). The mixture was degassed while applying vigorous stirring. The mixture was dispensed into cylindrical molds, polymerized at 30° C. for 10 hours, and post-cured at 100° C. for 5 hours. The copolymer was then removed from the molds and formed into blanks. The mechanical formation process comprised cutting the polymer into cylinders of 0.5 to 0.65 inches (1.27 to 1.65 cm.) in diameter and 0.1 to 0.2 inches (0.25 to 0.51 cm.) in thickness. The blanks were further cured at 100° C. for 5 hours. After curing, the blanks were ground to the desired dimensions.

Example 6

712.5 grams of EOEMA were mixed with 37.5 grams of EEEA, 3.75 grams of TMPTMA and 3.75 grams of ethylene glycol dimethacrylate (EGDMA). The mixture was degassed while applying vigorous stirring. The mixture was dispensed into cylindrical molds, polymerized at 30° C. for 10 hours, and post-cured at 100° C. for 5 hours. The copolymer was then removed from the molds and formed into blanks. The mechanical formation process comprised cutting the polymer into cylinders of 0.5 to 0.65 inches (1.27 to 1.65 cm.) in diameter and 0.1 to 0.2 inches (0.25 to 0.51 cm.) in thickness. The blanks were further cured at 100° C. for 5 hours. After curing, the blanks were ground to the desired dimensions.

Procedures for Machining Copolymers

Sample optics were cut using a DAC lathe with a freezing device attached to the collet of a DAC-Vision lathe. The freezing apparatus allowed polymer blanks to be affixed to a steel mandrel using moisture/ice. Freezing served two purposes: 1) it cooled the acrylic rubber to below its $T_g$ allowing for ease of cutting of the surface and 2) it allowed the icy surface to fix the blank in position for cutting. All materials will exhibit an optimal temperature for this operation which may vary as known by those skilled in the art, but will always be below the $T_g$ of the copolymer. For examples 7 through 10, the following conditions were used. The rough and fine tools consisted of single point diamond tools 0.5 mm and 0.3 mm in radius, respectively. The cooling device blank surface temperature was −5° C., and the DAC lathe run parameters used are listed in the following table:

|  | Rough Tool | Fine Tool |
| --- | --- | --- |
| Spindle Speed | 10,000 rpm | 9,500 rpm |
| Feed Rate | 0.66 in/min | 0.33 in/min |
| Depth of Cut | 0.2 mm | 0.07 mm |

The present compositions can have any or all of the components described herein. Likewise, the present methods can be carried out by performing any of the steps described herein, either alone or in various combinations. One skilled in the art will recognize that all embodiments of the present invention are capable of use with all other appropriate embodiments of the invention described herein. Additionally, one skilled in the art will realize that the present invention also encompasses variations of the present probes, configurations and methods that specifically exclude one or more of the components or steps described herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

All references, patents and publications disclosed herein are specifically incorporated by reference in their entireties and for all purposes as if fully set forth in their entireties. Unless otherwise specified, "a" or "an" means "one or more".

While preferred embodiments have been illustrated and described, it should be understood that changes and modifications can be made therein in accordance with ordinary skill in the art without departing from the invention in its broader aspects as defined in the following claims.

What is claimed is:

1. An intraocular lens comprising an optic portion and one or more haptic portions, wherein the optic portion comprises a copolymer consisting essentially of monomeric subunits, wherein the monomeric subunits consist essentially of:
   (a) one or more hydrophobic alkoxyalkoxyalkyl methacrylate or alkoxyalkoxyalkyl acrylate monomers, which can be the same or different, and/or one or more hydrophobic alkyl methacrylate or alkyl acrylate monomers; and
   (b) one or more alkoxyalkyl methacrylate monomers, which can be the same or different, and/or one or more alkoxyalkyl acrylate monomers, which can be the same or different, and
   further wherein the primary monomeric subunits of the copolymer by weight are the one or more alkoxyalkyl methacrylate and/or the one or more alkoxyalkyl acrylate monomers, and still further wherein the copolymer has an equilibrium water content of less than 5 percent by weight, and still further wherein the monomeric subunits comprise 1% or less of aromatic monomer, and wherein the copolymer is not a hydrogel.

2. The intraocular lens of claim 1, wherein the optic portion and the one or more haptic portions are made of the same copolymer.

3. The intraocular lens of the claim 2, wherein the optic portion and the one or more haptic portions are part of a one piece intraocular lens.

4. The intraocular lens of claim 1, wherein the optic portion and the one or more haptic portions are made of different materials.

5. The intraocular lens of claim 1, wherein the optic portion and the one or more haptic portions form a multiple piece intraocular lens.

6. The intraocular lens of claim 1, further comprising a polymer surrounding the copolymer wherein the polymer is not the same as the copolymer and the copolymer forms a core of the optic portion.

7. The intraocular lens of claim 1, wherein the lens has a central thickness of up to 1 mm and unfolds in less than or about 2 minutes when placed in a saline solution at a temperature of 36° C.

8. The intraocular lens of claim 7, wherein the lens unfolds in less than 1 minute when placed in a saline solution at a temperature of 36° C.

9. The intraocular lens of claim 7, wherein the lens unfolds in less than or about 30 seconds when placed in a saline solution at a temperature of 36° C.

10. A blank for the intraocular lens of claim 1.

11. An intraocular lens comprising an optic portion and one or more haptic portions, wherein the optic portion consists essentially of:
    (a) one or more hydrophobic monomers, which can be the same or different; and
    (b) one or more alkoxyalkyl methacrylate monomers, which can be the same or different, and/or one or more alkoxyalkyl acrylate monomers, which can be the same or different,
    further wherein the one or more alkoxyalkyl methacrylate monomers and/or the one or more alkoxyalkyl acrylate monomers comprise about 75 to about 97 percent of the copolymer by weight and the one or more hydrophobic monomers comprise about 3 to about 15 percent of the copolymer by weight,
    further wherein at least one of the hydrophobic monomers is a $C_1$ alkyl to $C_{15}$ alkyl methacrylate,
    and further wherein the optic portion comprises less than 1% of aromatic monomer, and
    wherein the copolymer is not a hydrogel.

12. The intraocular lens of claim 1, wherein said lens is a molded lens.

13. The intraocular lens of claim 1, wherein said lens is a fully molded lens.

14. The intraocular lens of claim 1, wherein the lens comprises an optic portion, and the lens is made by molding to form part of the optic portion of the lens.

15. The intraocular lens of claim 1, wherein the monomeric subunits do not comprise aromatic monomer.

16. The intraocular lens of claim 11, wherein the optic portion does not comprise aromatic monomer.

17. The intraocular lens of claim 1, wherein the copolymer has an equilibrium water content of less than 3 percent by weight.

* * * * *